United States Patent
Chandrashekhar et al.

(10) Patent No.: US 10,993,952 B2
(45) Date of Patent: May 4, 2021

(54) STABLE READY TO USE CYCLOPHOSPHAMIDE LIQUID FORMULATIONS

(71) Applicant: LEIUTIS PHARMACEUTICALS PVT. LTD., Hyderabad (IN)

(72) Inventors: Kocherlakota Chandrashekhar, Secunderabad (IN); Banda Nagaraju, Hyderabad (IN)

(73) Assignee: LEIUTIS PHARMACEUTICALS PVT. LTD., Hyderabad (IN)

( * ) Notice: Subject to any disclaimer, the term of this patent is extended or adjusted under 35 U.S.C. 154(b) by 0 days.

(21) Appl. No.: 15/551,507

(22) PCT Filed: Feb. 15, 2016

(86) PCT No.: PCT/IB2016/050788
§ 371 (c)(1),
(2) Date: Aug. 16, 2017

(87) PCT Pub. No.: WO2016/132270
PCT Pub. Date: Aug. 25, 2016

(65) Prior Publication Data
US 2018/0055861 A1    Mar. 1, 2018

(30) Foreign Application Priority Data

Feb. 16, 2015   (IN) .............................. 735/CHE/2015
Jun. 22, 2015   (IN) .......................... 3117/CHE/2015

(51) Int. Cl.
| | | |
|---|---|---|
| A61K 31/675 | (2006.01) | |
| A61K 47/10 | (2017.01) | |
| A61K 9/08 | (2006.01) | |
| A61K 9/00 | (2006.01) | |

(52) U.S. Cl.
CPC .......... *A61K 31/675* (2013.01); *A61K 9/0019* (2013.01); *A61K 9/08* (2013.01); *A61K 47/10* (2013.01)

(58) Field of Classification Search
CPC .... A61K 31/675; A61K 31/66; A61K 9/0019; A61K 9/08; A61K 47/10
USPC ......................................................... 514/110
See application file for complete search history.

(56) References Cited

U.S. PATENT DOCUMENTS

| | | | | |
|---|---|---|---|---|
| 4,879,286 | A * | 11/1989 | Alam .................. | A61K 9/0019 514/110 |
| 4,952,575 | A * | 8/1990 | Sauerbier ............. | A61K 9/0019 514/110 |
| 2013/0172271 | A1* | 7/2013 | Fragale ................. | A61K 38/12 514/21.1 |
| 2015/0320775 | A1* | 11/2015 | Palepu .................. | A61K 47/10 514/110 |

FOREIGN PATENT DOCUMENTS

WO    2014/068585 A1    5/2014

OTHER PUBLICATIONS

Beijen et al. Journal of Parenteral Science & Technology 1992, 46 (4), 111-116, full text.*
International Search Report and Written Opinion of the International Searching Authority for PCT/IB2016/050788 dated Jun. 27, 2016.
Beijnen, J.H., et al., "Chemical stability of two sterile, parenteral formulations of cyclophosphamide (Endoxan) after reconstitution and dilution in commonly used infusion fluids." J Parenter Sci Technol., vol. 46, No. 4, pp. 111-116, Abstract (1992).

* cited by examiner

*Primary Examiner* — Irina Neagu
(74) *Attorney, Agent, or Firm* — Sughrue Mion, PLLC

(57) ABSTRACT

The present invention relates to stable ready to use liquid formulations of Cyclophosphamide for parenteral use. The ready to use composition comprises Cyclophosphamide dissolved in a solvent system comprising a solvent, cosolvent(s) and antioxidant(s).

4 Claims, No Drawings

STABLE READY TO USE CYCLOPHOSPHAMIDE LIQUID FORMULATIONS

FIELD OF INVENTION

The invention relates to stable ready to use, liquid parenteral formulations of Cyclophosphamide and process of preparation thereof.

BACKGROUND OF THE INVENTION

Cyclophosphamide is chemically known as 2-[bis(2-chloroethyl)amino]tetrahydro-2H-1,3,2-oxazaphosphorine 2-oxide and has the following structure:

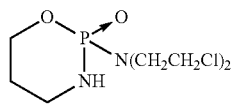

Cyclophosphamide was one example of a group of novel cyclic phosphoric acid ester amides which were disclosed and claimed in U.S. Pat. No. 3,018,302 granted on Jan. 23, 1962 to H. Arnold, et al.

The published literature and earlier patent applications of Cyclophosphamide deal with lyophilized compositions of the drug. U.S. Pat. No. 4,537,883 to Alexander et al. disclose various lyophilizates of Cyclophosphamide prepared by lyophilizing a solution of Cyclophosphamide and one or more excipients and re-hydrating the product such that it contains about 4% moisture. Kovalcik et al. have examined the stability of Cyclophosphamide in lyophilized cakes containing mannitol, lactose and sodium bicarbonate (first paper) and urea, polyvinylpyrrolidone and dextran (second paper). (Journal of Parenteral Science & Technology 42(1) pp 29-37 and 42(5) pp 165-173).

More recent patent applications also deal with various lyophilized formulations of Cyclophosphamide. WO1994008592A1 to Hannu et al. describes storage-stable lyophilized Cyclophosphamide composition comprising Cyclophosphamide and dextran. U.S. Pat. No. 5,418,223 to Palepu et al. describes a method for lyophilizing Cyclophosphamide which overcomes the need to add water back to the lyophilizate to stabilize it. U.S. Pat. No. 5,130,305 to Palepu et al. describes a lyophilized Cyclophosphamide composition comprising Cyclophosphamide, sodium bicarbonate, and water.

Cyclophosphamide is available as monohydrate in parenteral dosage formulation consisting of sterile packaged dry powder blend mixtures of drug and sodium chloride. The premixes were dissolved in water prior to administration. During the processing and storage of dry powder premix formulation, a glassiness and or stickiness could be acquired by the premix composition giving the material an unattractive appearance and with inferior solubility characteristics and decreased potency.

All the formulations known earlier and described in literature require reconstitution with a diluent liquid which decreases the ease of administration. Moreover the reconstituted and diluted solutions can be stored only for a fixed period of time without compromising the quality of the product.

Hence there is a need to develop formulations of Cyclophosphamide overcoming the disadvantages of products and processes known in the art

SUMMARY OF THE INVENTION

One object of the invention is to provide a stable ready to use, liquid parenteral formulation of Cyclophosphamide with less than 0.5% each of Impurity A, B, and D. Another aspect of the invention is to provide stable ready to use, liquid parenteral formulation of Cyclophosphamide comprising one or more solvents and other pharmaceutically acceptable adjuvants thereof.

Yet another aspect of the invention is to provide stable ready to use, liquid parenteral formulation of Cyclophosphamide comprising one or more solvents selected from ethanol, propylene glycol, polyethylene glycol, water, dimethylacetamide, glycerol and anti-oxidant such as monothioglycerol, butylated hydroxyanisole, butylated hydroxyl toluene, citric acid, L-cysteine, ascorbic acid and the like.

Yet another aspect of the invention is to provide the optimised concentration of Cyclophosphamide and solvents to provide a stable ready to use Cyclophosphamide formulation.

DETAILED DESCRIPTION OF THE INVENTION

In the context of this invention "Cyclophosphamide" refers to the pharmaceutically acceptable salts, solvates, hydrates and anhydrous forms thereof, preferably Cyclophosphamide monohydrate.

As used herein, "ready to use Cyclophosphamide" formulations refers to formulations that contain Cyclophosphamide in dissolved or solubilised form and are to be intended to be used as such or upon further dilution in intravenous diluents.

Cyclophosphamide is known to be susceptible to hydrolysis. Therefore it is supplied as a lyophilised formulation to reduce the formation of impurities and to improve the stability of the final formulation.

The inventors have discovered a stable ready to use, liquid parenteral formulations of Cyclophosphamide which is stable and has impurities controlled within the acceptable limits. The impurities formed by the hydrolytic degradation of Cyclophosphamide are designated as Impurity A, B and D. These impurities are structurally identified and described in the art.

Impurity A Bis(2-chloroethyl)amine hydrochloride

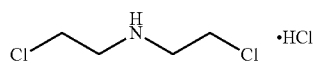

Impurity B 3-(2-Chloroethyl)-2-oxo-2-hydroxy-1,3,6,2-oxadiazaphosphonane

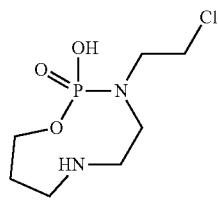 [SMILES: O=P1(O)OCCCNCCN1CCCl]

Impurity D 3-[2-(2-Chloroethylamino)ethylamino] propyl dihydrogen phosphate dihydrochloride

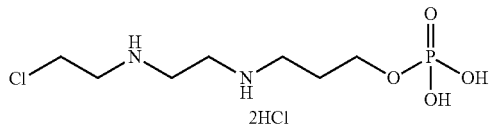 [SMILES: O=P(O)(O)OCCCNCCNCCCl]

In the first aspect of the invention, ready to use Cyclophosphamide formulations with excellent storage stability are described. The formulations of the present invention are tested for stability after being stored at 40° C., 75% RH for 7 days.

The formulations show less than 0.5% each of impurities A, B and D, more preferably less than 0.4% each of impurities A, B and D.

The inventive compositions of Cyclophosphamide were found to be stable when stored at 2° C. to 8° C. temperature.

In the second aspect of the invention, ready to use formulations of Cyclophosphamide are described. These compositions comprise Cyclophosphamide monohydrate, one or more solvents and optionally an antioxidant.

Solvents can be selected from the group comprising alcohols such as ethanol, propylene glycol, polyethyleneglycol, glycerol, glycofurol, tertiary butyl alcohol, diethylene glycol monoethyl ether, water, dimethylacetamide, aqueous solutions of disaccharides and mixtures thereof. The quantity of solvents ranges from about 40-99% by weight of the composition.

The antioxidant, may be selected from the group of sulphur containing antioxidants, butylated hydroxyanisole, butylated hydroxyl toluene, citric acid, lactic acid, benzoic acid, tocopherol, monothioglycerol, ascorbic acid, L-cysteine, methyl paraben, benzyl alcohol, propyl gallate, thioglycolic acid, tartaric acid, thiodipropionic acid, complexing agents, aminoacids and the like. The concentration of the antioxidant used is less than 5%, more preferably less than 3% by weight of the composition.

In one preferred embodiment, the liquid formulations of Cyclophosphamide comprise one or more solvents selected from alcohols such as ethanol, polyethylene glycol, propylene glycol, glycerol, water, and an antioxidant selected from monothioglycerol, butylated hydroxyanisole, butylated hydroxyl toluene, citric acid, L-cysteine, ascorbic acid and the like.

The preferred embodiment of stable liquid parenteral formulation of Cyclophosphamide comprises:

| | | |
|---|---|---|
| (i) | Cyclophosphamide | 5-40% |
| (ii) | Polyethylene glycol | 0-30% |
| (iii) | Ethanol | 20-98% |
| (iv) | Propylene glycol | 0-20% |
| (v) | Optionally other pharmaceutically acceptable adjuvants thereof. | |

The most preferred embodiment of stable ready to use, liquid parenteral formulation of Cyclophosphamide comprises:

| | | |
|---|---|---|
| (i) | Cyclophosphamide | 6-30% |
| (ii) | Polyethylene glycol | 0-25% |
| (iii) | Ethanol | 40-92% |
| (iv) | Propylene glycol | 0-15% |
| (v) | Water for Injection | 0-20% |
| (vi) | Antioxidant | <3% |

The invention further relates to a process of preparing ready to use liquid parenteral formulation of Cyclophosphamide comprising:
i. Addition of Cyclophosphamide to the solvent/solvents.
ii. Addition of anti-oxidant to the solution followed by stirring till uniform solution is obtained.
iii. Filtering and filling of the solution in suitable container or vials followed by stoppering and sealing of the vials.

Cyclophosphamide formulations prepared according to the invention were tested for stability under accelerated condition for a period of 1 week at 40° C./75% RH. The stability data of the invention formulation is summarized in table 1.

TABLE 1

Stability data of the invention formulation

| | | Stability Data at 40° C./75% RH | | | | |
|---|---|---|---|---|---|---|
| | | Example 2 | | Example 4 | | Example 5 |
| S. No. | Impurities | Initial | 1 Week | Initial | 1 Week | 1 Week |
| | | Impurities (% w/w) | | | | |
| 1 | Impurity-A | ND | ND | 0.01 | 0.05 | ND |
| 2 | Impurity-B | 0.06 | 0.18 | 0.05 | 0.19 | 0.21 |
| 3 | Impurity-D | ND | ND | ND | ND | ND |
| 4 | Impurity-E | ND | ND | ND | 0.45 | 0.65 |
| 5 | Impurity-G | ND | ND | ND | 1.24 | 1.22 |
| 6 | Total | 0.07 | 1.87 | 0.06 | 2.01 | 2.33 |
| 7 | Assay (%) | 101.6 | 101.9 | 102.1 | 98.9 | 99.7 |

ND: Not detectable

Surprisingly no significant increase of impurities A, B and D was observed even at accelerated conditions. The data confirms the inventors' finding that the use of suitable solvents in suitable proportions and an anti-oxidant yield best results.

The following examples further describe certain specific aspects and embodiments of the present invention and demonstrate the practice and advantages thereof. It is to be understood that the examples are given by way of illustration only and are not intended to limit the scope of the invention in any manner.

EXAMPLES

Example 1

| | | Qty/vial | | |
|---|---|---|---|---|
| S. No | Ingredients | 500 mg | 1 g | 2 g |
| 1 | Cyclophosphamide | 500 mg | 1.0 g | 2.0 g |
| 2 | PEG 400 | 0.415 g | 0.83 g | 1.66 g |
| 3 | Ethanol (99%) | 3.54 g | 7.08 g | 14.16 g |
| 4 | Propylene glycol | 0.21 g | 0.42 g | 0.84 g |
| 5 | Monothioglycerol | 0.345 mg | 0.69 mg | 1.39 mg |

Manufacturing Process:
Cyclophosphamide was added to the compounding vessel containing ethanol. PEG-400 was added and stirred till a uniform solution was obtained. Propylene glycol was added, followed by the addition of monothioglycerol and stirred till a uniform solution was obtained. The solution was filtered, followed by stoppering and sealing of the vials.

Example 2

| S. No | Ingredients | Qty/vial |
|---|---|---|
| 1 | Cyclophosphamide | 1.0 g |
| 2 | PEG 400 | 0.733 g |
| 3 | Ethanol | 6.23 g |
| 4 | Propylene glycol | 0.367 g |
| 5 | Monothioglycerol | 0.69 mg |

Manufacturing Process:

Cyclophosphamide was added to the compounding vessel containing ethanol. PEG-400 was added and stirred till a uniform solution was formed. Propylene glycol was added, followed by the addition of monothioglycerol and stirred till a uniform solution was obtained. The solution was filtered, followed by stoppering and sealing of the vials.

Example 3

| | | Qty/vial | |
|---|---|---|---|
| S. No | Ingredients | 500 mg | 1 g | 2 g |
| 1 | Cyclophosphamide | 500 mg | 1.0 g | 2.0 g |
| 2 | Ethanol | 3.54 g | 7.08 g | 14.16 g |
| 3 | Propylene glycol | 0.21 g | 0.42 g | 0.84 g |
| 4 | Monothioglycerol | 7.5 mg | 15 mg | 30 mg |

Manufacturing Process:

Cyclophosphamide was added to the compounding vessel containing ethanol. Propylene glycol was added, followed by the addition of monothioglycerol and stirred till a uniform solution was obtained. The solution was filtered, followed by stoppering and sealing of the vials.

Example 4

| S. No | Ingredients | Qty/vial |
|---|---|---|
| 1 | Cyclophosphamide | 1.00 g |
| 2 | PEG-400 | 0.310 g |
| 3 | Ethanol | 6.95 g |
| 4 | Monothioglycerol | 0.69 mg |

Manufacturing Process:

Cyclophosphamide was added to the compounding vessel containing ethanol. PEG-400 was added followed by the addition of monothioglycerol and stirred till a uniform solution was obtained. The solution was filtered, followed by stoppering and sealing of the vials. pH of the solution was around 3.0.

Example 5

| S. No | Ingredients | Qty/vial |
|---|---|---|
| 1 | Cyclophosphamide | 1.00 g |
| 2 | PEG-400 | 0.15 g |
| 3 | Ethanol | 3.15 g |
| 4 | Monothioglycerol | 0.69 mg |

Manufacturing Process:

Cyclophosphamide was added to the compounding vessel containing ethanol. PEG-400 was added followed by the addition of monothioglycerol and stirred till a uniform solution was formed. The obtained solution was filtered, followed by stoppering and sealing of the vials.

Example 6

| S. No | Ingredients | Qty/vial |
|---|---|---|
| 1. | Cyclophosphamide | 1000 mg |
| 2. | PEG-400 | 0.15 g |
| 3. | Ethanol | 3.12 g |
| 4. | Propylene glycol | 0.15 g |
| 5. | Monothioglycerol | 0.69 mg |

Manufacturing Process:

Cyclophosphamide was added to the compounding vessel containing ethanol. PEG-400 was added followed by the addition of propylene glycol. Monothioglycerol was added and stirred till a uniform solution was obtained. The solution was filtered, followed by stoppering and sealing of the vials. The process was carried out at 2-8° C.

Example 7

| S. No | Ingredients | Qty/vial |
|---|---|---|
| 1. | Cyclophosphamide | 1000 mg |
| 2. | PEG-400 | 0.30 g |
| 3. | Ethanol (Absolute) | 3.12 g |
| 4. | Monothioglycerol | 0.69 mg |

Manufacturing Process:

Cyclophosphamide was added to the compounding vessel containing ethanol. PEG-400 was added followed by addition monothioglycerol and stirred till a uniform solution was obtained. The solution was filtered, followed by stoppering and sealing of the vials.

Example 8

| S. No | Ingredients | Qty/vial |
|---|---|---|
| 1. | Cyclophosphamide | 1000 mg |
| 2. | PEG-400 | 0.15 g |
| 3. | Ethanol | 3.1 g |
| 4. | Propylene glycol | 0.15 g |
| 5. | Water for Injection | 20 mg |
| 6. | Monothioglycerol | 0.69 mg |

Manufacturing Process:

Cyclophosphamide was added to the compounding vessel containing ethanol. PEG-400 was added and stirred till a uniform solution was formed. Propylene glycol was added followed by the addition of monothioglycerol and water and stirred till a uniform solution was obtained. The solution was filtered, followed by stoppering and sealing of the vials.

We claim:

1. A stable liquid parenteral formulation of cyclophosphamide comprising
    i) cyclophosphamide in a concentration of about 12% to about 23% based on total formulation weight;
    ii) an ethanol content of about 70% to about 75% based on total formulation weight;
    iii) both polyethylene glycol and propylene glycol, wherein a polyethylene glycol to propylene glycol mass ratio is between approximately 1.0:1.0 to approximately 2.0:1.0; and
    iv) about 3.4% to about 8.8% based on total formulation weight of polyethylene glycol
    v) about 3.4% to about 4.4% based on total formulation weight of propylene glycol
    vi) wherein, after storage for 7 days at 40° C./75% RH, decomposition to form any of the following impurities is less than 0.5%:
        a) bis(2-chloroethyl)amine hydrochloride;
        b) 3-(2-chloroethyl)-2-oxo-2-hydroxy-1,3,6,2-oxadiazaphosphonane; and
        c) 3-[2-(2-chloroethylamino)ethyl amino] propyl dihydrogen phosphate dihydrochloride.

2. The formulation of claim 1, further comprising an antioxidant.

3. The formulation of claim 2, wherein the antioxidant is monothioglycerol at concentration of about 0.01% to about 0.02% by total formulation weight.

4. A stable liquid parenteral formulation of cyclophosphamide comprising
    i. cyclophosphamide in a concentration of about 23% based on total formulation weight
    ii. an ethanol content of about 70% based on total formulation weight;
    iii. both polyethylene glycol and propylene glycol, wherein a polyethylene glycol to propylene glycol mass ratio is about 1.0:1.0; and
    iv. about 3.4% to about 8.8% based on total formulation weight of polyethylene glycol
    v. about 3.4% to about 4.4% based on total formulation weight of propylene glycol, and
    vi. about 0.02% based on total formulation weight of monothioglycerol.

* * * * *